United States Patent
McCarthy et al.

(10) Patent No.: US 7,159,593 B2
(45) Date of Patent: Jan. 9, 2007

(54) METHODS FOR REDUCTION OF PRESSURE EFFECTS OF CARDIAC TRICUSPID VALVE REGURGITATION

(75) Inventors: Patrick M. McCarthy, Hunting Valley, OH (US); Rodolfo C. Quijano Quijano, Laguna Hills, CA (US)

(73) Assignee: 3F Therapeutics, Inc., Lake Forest, CA (US)

( * ) Notice: Subject to any disclaimer, the term of this patent is extended or adjusted under 35 U.S.C. 154(b) by 13 days.

(21) Appl. No.: 10/418,663

(22) Filed: Apr. 17, 2003

(65) Prior Publication Data

US 2004/0206363 A1    Oct. 21, 2004

(51) Int. Cl.
*A61B 19/00*    (2006.01)
*A61F 2/06*    (2006.01)

(52) U.S. Cl. ..................... 128/898; 623/1.24
(58) Field of Classification Search ............... 128/898; 623/1.24
See application file for complete search history.

(56) References Cited

U.S. PATENT DOCUMENTS

| | | | |
|---|---|---|---|
| 4,806,595 A | 2/1989 | Noishiki et al. | |
| 5,607,465 A | 3/1997 | Camilli | |
| 5,824,061 A | 10/1998 | Quijano et al. | |
| 5,855,601 A | 1/1999 | Bessler et al. | |
| 5,928,181 A | 7/1999 | Coleman | |
| 5,954,766 A | 9/1999 | Zadno-Azizi | |
| 5,957,949 A | 9/1999 | Leonhardt | |
| 5,997,573 A | 12/1999 | Quijano et al. | |
| 6,007,575 A | 12/1999 | Samuels | |
| 6,299,637 B1 | 10/2001 | Shaolian et al. | |
| 6,383,193 B1 | 5/2002 | Cathcart et al. | |
| 6,451,025 B1 | 9/2002 | Jervis | |
| 6,503,272 B1 | 1/2003 | Duerig et al. | |
| 6,517,573 B1 | 2/2003 | Pollock | |
| 2003/0135255 A1 | 7/2003 | Sundar | |
| 2003/0163194 A1 | 8/2003 | Quijano | |

FOREIGN PATENT DOCUMENTS

WO    WO 200217819 A2 *    3/2002

OTHER PUBLICATIONS

Klablunde, Richard E. "Cardiovascular Physiology Concepts", Dec. 6, 2002 http://web.archive.org/web/20021206150630/http://www.cvphysiology.com/Heart+Disease/HD005.htm.*

* cited by examiner

*Primary Examiner*—Tom Barrett
(74) *Attorney, Agent, or Firm*—Barbara A. Wrigley; Oppenheimer Wolff & Donnelly LLP

(57) ABSTRACT

A method of protecting an upper body and a lower body of a patient from high venous pressures comprising implanting a first stented valve at the superior vena cava and a second stented valve at the inferior vena cava, wherein the first and second valves are configured to permit blood flow towards a right atrium of the patient and prevent blood flow in an opposite direction.

20 Claims, 2 Drawing Sheets

METHODS FOR REDUCTION OF PRESSURE EFFECTS OF CARDIAC TRICUSPID VALVE REGURGITATION

FIELD OF THE INVENTION

The present invention relates generally to methods of using stented venous valves and, more particularly, to methods for reduction of pressure effects of cardiac tricuspid valve regurgitation by implanting stented valve bioprostheses at vena cava locations.

BACKGROUND OF THE INVENTION

Among the quadruped heart valves in a human body, the tricuspid valve separates the right atrium (upper chamber) from the right ventricle (lower chamber), and channels the venous blood return to the heart on its way to the lungs. When the venous blood is impelled to the lung arteries, this tricuspid valve closes to block the blood return from backflowing to the atrium and thus provides efficiency to the ejection of blood from the right ventricle that directs the flow towards the lung. In instances where the tricuspid valve is unable to close properly, the pumping pressure of the ventricle can be transmitted in reverse to the atrium and subsequently to the vena cavae. Typically, the superior vena cava functions to bring blood to the heart from the head and the inferior vena cava functions to bring blood to the heart from the liver and other parts of the body (kidneys, gut, legs) that are located below the heart. This pressure can have deleterious effects on the work of the heart and circulatory system. The device herein described provides means of reduction or total nullification of the effects of pressure on the channels of venous return to the heart.

The tricuspid heart valve has an area close to 10 square centimeters, and a circumference approaching 12 centimeters. As the name implies it has three cusps or leaflets that separate to open the valve and allow the venous return from the body to the heart to enter the pumping chamber or right ventricle that redirects the flow towards the lung where venous blood is oxygenated and transformed into arterial blood to supply all tissues of the body. During the pumping action, the tricuspid valve closes to impede retrograde flow into the right atrium.

Acquired disease of the tricuspid valve is much less common than that of the other valves of the heart; this is a reflection of the lower pressures that are experienced by the right chambers of the heart, and thus, the valves of the right side of the heart function generally under less stresses than its left side counterparts. Disease can affect the tricuspid valve mostly in two forms, 1) as tricuspid valve stenosis, a restriction of the opening of the valve, most likely of rheumatic origin, and 2) as tricuspid valve regurgitation or incompetence, generally due to any disease process that causes alterations in the tricuspid valve apparatus that consists of: leaflets, chords, tendinous material that join the leaflet to the muscle of the right side of the heart, or the annulus (the ring of tissue where the leaflets join the atrium). In the latter, the valve is unable to close completely thus allowing retrograde flow or regurgitation from the ventricle into the atrium.

A small degree of tricuspid regurgitation is found in normal hearts and the prevalence increases with age. Physiologically, the regurgitation is seen as a jet whose velocity is proportional to the pressure differential between the right ventricle and the right atrium. Tricuspid regurgitation (TR) alone may be well tolerated. However, patients suffering from severe TR are troubled with swelling of the legs, pulsations of the jugular vein pulse at the neck due to reverse flow and pressure into the superior vena cava. Other problems associated with severe TR include liver congestion due to reverse pressure to the inferior vena cava and the liver veins, and fatigue and general malaise because of decreased pumping of blood through the heart (that is, decreased cardiac output), that may progress to cardiac cirrhosis and liver dysfunction with prolonged hepatic congestion. Furthermore, high venous pressure may contribute to renal dysfunction and other symptoms of abdominal bloating. All these findings are dependent on the severity of tricuspid regurgitation and pulmonary hypertension. Often the end effect is right heart failure.

Tricuspid regurgitation can be alleviated or eliminated by surgical means, either by replacement of the total valve apparatus with an artificially fabricated replacement tricuspid heart valve, or by constriction of the valve ring with means of an annular remodeling ring (annuloplasty ring). The tricuspid valve repair is not always 100% effective in eliminating the TR, as it has been found in some instances that patients (up to about 15%) who have undergone tricuspid valve annuloplasty may leave the hospital with moderate to severe TR and the tricuspid dysfunction rate may steadily increase to about 30–50%. If surgery is impossible to perform, i.e., if the patient is deemed inoperable or operable only at a too high surgical risk, an alternative possibility is to treat the patient with a stented valvular device and percutaneous means of device delivery for protecting the upper and lower body from high venous pressures.

U.S. Pat. No. 6,503,272 issued on Jan. 7, 2003, entire contents of which are incorporated herein by reference, discloses an artificial venous valve which incorporates a stent having one or more of the elements comprising its frame deformed inwardly towards its center and a biocompatible fabric attached to the one or more elements utilized to replace or supplement incompetent or damaged venous valves.

U.S. Pat. No. 5,855,601 issued on Jan. 5, 1999, entire contents of which are incorporated herein by reference, discloses an artificial venous valve comprising a tubular valve segment containing venous valve means and at least one self-expanding, cylindrical stent member having a plurality of barbs extending from the outer surface of the stent member to engage the natural tissue of the site to hold the valve in place after implantation.

U.S. Pat. No. 6,299,637 issued on Oct. 9, 2001, entire contents of which are incorporated herein by reference, discloses a self expandable prosthetic venous valve comprising a tubular wire support, expandable from a first reduced diameter to a second enlarged diameter, and at least one leaflet pivotably positioned in the flow path for permitting flow in a forward direction and resisting flow in a reverse direction.

U.S. Pat. No. 5,824,061 issued on Oct. 20, 1998, entire contents of which are incorporated herein by reference, discloses an endovascular venous valve prosthesis comprising an endovascular stent assembly including a stent having a generally cylindrical body with a hollow bore extending longitudinally therethrough and first and second support struts formed on opposite sides of the outflow end of the cylindrical body and extending generally longitudinally therefrom; and a preserved segment of vein having an outer wall and a venous valve positioned therein, the valve having two leaflets extending generally longitudinally within the segment of vein with lateral edges adjacent the outer wall.

U.S. Pat. No. 5,607,465 issued on Mar. 4, 1997, entire contents of which are incorporated herein by reference, discloses a valve for use in a blood vessel having a bent flexible wire mesh with elasticity and plasticity so as to be collapsible and implantable remotely at a desired site and a monocusp sail-like valving element mounted onto it.

U.S. Pat. No. 5,997,573 issued on Dec. 7, 1999, entire contents of which are incorporated herein by reference, discloses a dilation restrictor apparatus for limiting the extent to which a blood vessel may dilate adjacent to a point whereat a cut end of the blood vessel has been anastomosed to a venous valve implant, the dilation restrictor apparatus comprising an elongate tubular body having a hollow bore containing a plurality of apertures formed therein to permit passage of fluid therethrough.

U.S. Pat. No. 6,383,193 issued on May 7, 2002, entire contents of which are incorporated herein by reference, discloses a delivery system for the percutaneous insertion of a self-expanding vena cava filter device being formed with a length along a longitudinal filter axis, the system comprising constraining the filter in a compact condition within an elongated, radially flexible and axially stiff tubular member and a displacement member attached to the tubular member for displacing the filter from the thereby to deploy the filter.

None of the above-referenced prior art discloses means for protecting the upper body and lower body of a patient from spiked or elevated venous pressure transmitted from the right atrium.

Therefore, it is one preferred object to provide a method of protecting an upper body and a lower body of a patient from high venous pressures comprising implanting a first stented valve at a superior vena cava and a second stented valve at an inferior vena cava, wherein the first and second valves are configured to permit blood flow towards the right atrium of the patient and prevent blood flow in an opposite direction.

SUMMARY OF THE INVENTION

In general, it is one object of the present invention to provide stented valve bioprostheses and methods for reduction of pressure effects of cardiac tricuspid valve regurgitation.

In some aspect of the invention, it is provided a method of protecting an upper body and a lower body of a patient from high venous pressures comprising implanting a first valve at the superior vena cava and a second valve at the inferior vena cava, wherein the first and second valves are configured to permit blood flow towards the right atrium of the patient and prevent blood flow in an opposite direction. In one embodiment, the first valve and/or the second valve is a stented valve, wherein the stented valve comprises a tissue valve secured to a support structure, and wherein the stent is collapsibly expandable.

In one aspect, the step of implantation is carried out by first implanting the first stented valve at the superior vena cava. In another aspect, the step of implanting is carried out by implanting the second valve at the inferior vena cava that is followed by implanting the first stented valve at the superior vena cava.

The tissue valve portion of the stented valve comprises at least one valve leaflet, wherein the leaflet is made from a pericardium, the pericardium may be selected from a group consisting of a bovine pericardium, an equine pericardium, a porcine pericardium, and an ovine pericardium. In another embodiment, the tissue valve is a porcine valve or a venous valve procured from a group consisting of a bovine jugular vein, an equine jugular vein, a porcine jugular vein, and an ovine jugular vein. The tissue valve is generally chemically treated with a chemical treating agent selected from a group consisting of glutaraldehyde, formaldehyde, dialdehyde starch, epoxy compounds, genipin, and mixture thereof.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The preferred embodiments of the present invention described below relate particularly to venous valve bioprostheses and methods for reduction of pressure effects of cardiac tricuspid valve regurgitation. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

A stented valve or valved stent is a device to be placed inside a channel of the body that allows fluid flow in one direction and prevents fluid flow in an opposite direction. In a normal person, the superior vena cava functions to bring blood to the heart from the head and the inferior vena cava functions to bring blood to the heart from the liver and other parts of the body (kidneys, gut, legs) that are located below the heart.

In instances where the tricuspid valve (54 in FIG. 4) is unable to close properly, the pumping pressure of the ventricle 53 can be transmitted in reverse to the atrium 52 and subsequently to the vena cavae 55, 56. This pressure can have deleterious effects on the work of the heart and circulatory system. It is one aspect of the invention to provide a device and methods enabling reduction or total nullification of the effects of elevated pressure on the channels of venous return to the heart.

Figure 1:
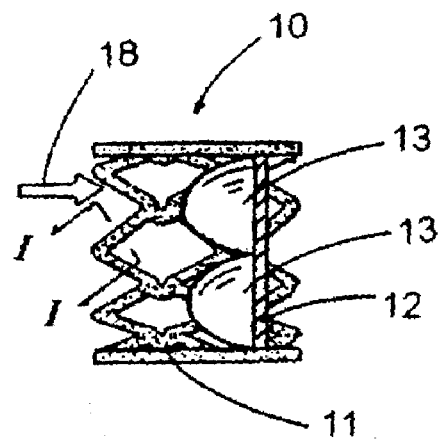
FIG. 1 is a front view of a stented valve according to the principles of the present invention.
Figure 2:
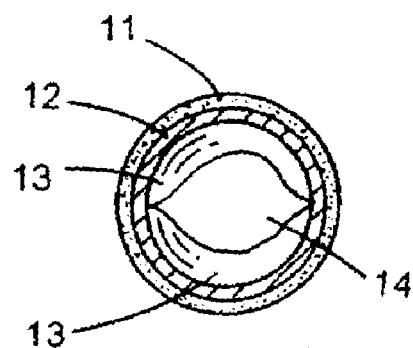
FIG. 2 is a side view of the stented valve of FIG. 1.

FIG. 1 shows a front view of a stented valve while FIG. 2 shows its side view according to the principles of the present invention. The stented valve 10 comprises a tissue valve secured to a support structure 11, wherein the support structure is collapsibly expandable. The tissue valve comprises at least one leaflet 13 securely attached to an annular base 12. The tissue valve is configured to permit fluid flow in a first direction (as shown by the arrow 18) and prevent fluid flow in an opposite direction. When the fluid flows in the first direction, the leaflet 13 is open having a flow-through opening 14.

In one embodiment, the support structure 11 of the stented valve 10 is self-expandable out of a delivery sheath. In operations, the stent is compressed radially to be held within the lumen of the delivery apparatus, sheath, catheter, applicator, or cannula. Upon delivery out of the apparatus, the stent self-expands to its pre-compressed state. The stent is typically made of a material selected from a group consisting of stainless steel, Nitinol, plastics or the like. In another embodiment, the stent 11 of the stented valve 10 is expandable by an inflatable balloon, which is well known to an ordinary artisan who is skilled in the art.

In still another embodiment, the support structure 11 is made of a shape-memory material having a first shape transition temperature of between about 30° C. and 45° C. and a second shape transition temperature of between about 5° C. and −10° C. In operations, the stent is collapsibly deformed to a small diameter and held at about or below 5° C., preferably between about 5° C. and −10° C. The deformed stent is then inserted within a delivery apparatus. During delivery, the stent is maintained at below the second shape transition temperature by flushing or contacting with super-cooled saline. At a desired location, the stent is pushed out of the sheath. Upon reaching the first shape transition temperature, the stent expands to lock itself in position.

The use of shape memory alloys or intermetallics and, specifically, Nitinol in the construction of medical devices is well known. U.S. Pat. No. 6,451,025 issued on Sep. 17, 2002, entire contents of which are incorporated herein by reference, discloses hysteresis behavior of Nitinol to generate shape change or force at or around constant body temperature by forming the device to the final shape desired, straining the device in a direction which tends to facilitate placement into the body, restraining the device in this strained shape during insertion into or placement near the body, then releasing all or part of the device such that it returns or tends to return to the desired shape with temperature activation.

Figure 4:
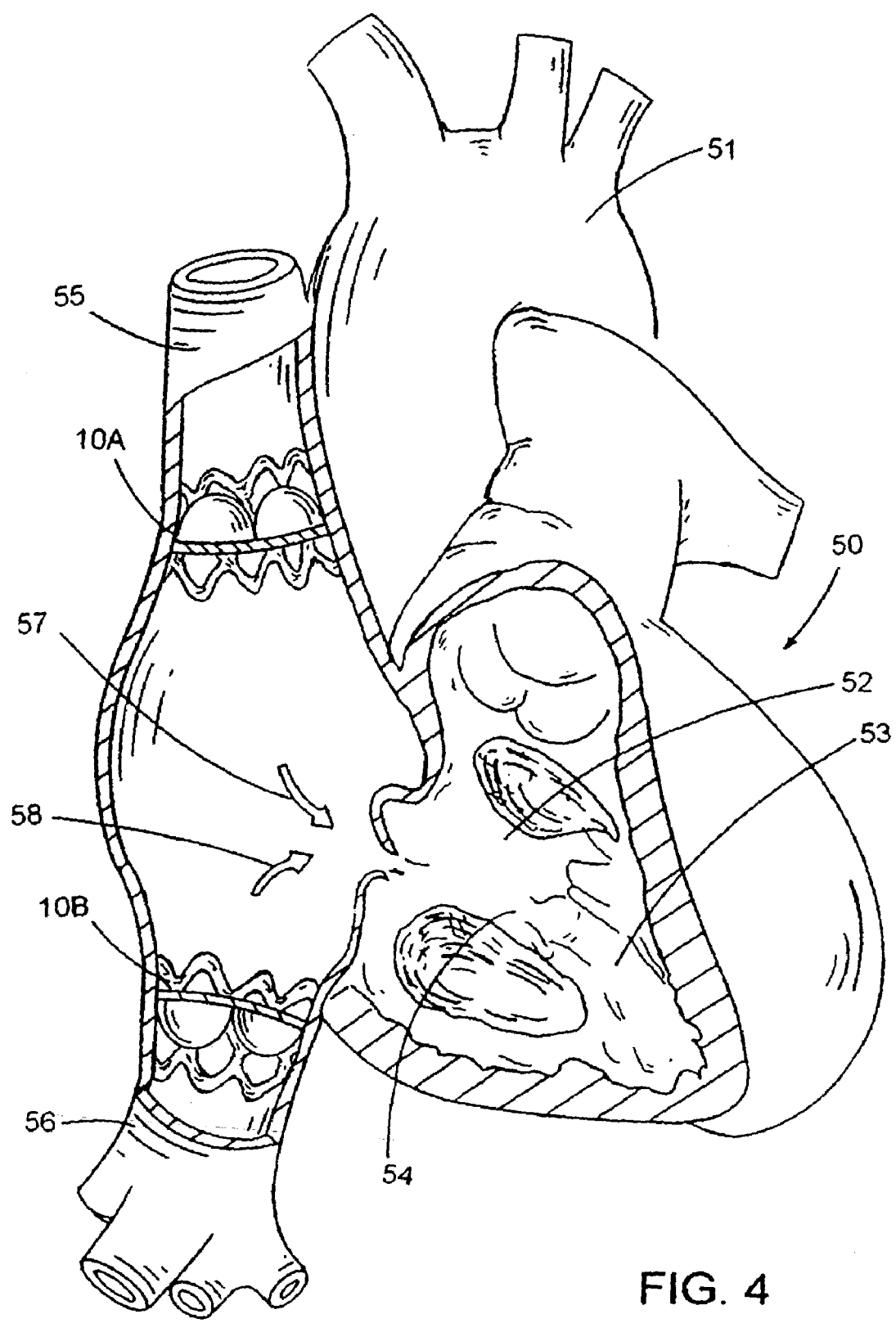
FIG. 4 is a procedure of implanting a stented valve at the superior vena cava and another stented valve at the inferior vena cava, wherein both valves are configured to permit blood flow towards the right atrium.

FIG. 4 shows a preferred embodiment of procedures of protecting an upper body and a lower body of a patient from high venous pressures, the method comprising implanting a first stented valve 10A at a superior vena cava 55 and a second stented valve 10B at an inferior vena cava 56, wherein the first valve 10A and the second valve 10B are configured to permit blood flow (as indicated by arrows 57, 58) towards a right atrium 52 of the heart 50 and prevent blood flow in an opposite direction. In a normal patient, the oxygenated blood is pumped from the heart 50 through aorta 51 to the body.

In one aspect, the first stented valve 10A is delivered to the superior vena cava 55 endoluminally, followed by delivering the second stented valve 10B to the inferior vena cava 56 endoluminally. In another aspect, the second stented valve is delivered first. The step of delivering either the first or the second stented valve endoluminally is through an incision at a blood vessel selected from a group consisting of a jugular vein, a femoral vein, and a subclavian vein. In a further aspect, the support structure 11 further comprises means for anchoring the stent onto surrounding tissue of either the superior vena cava or the inferior vena cava, for example hooks, barbs, needles, protrusion, or the like that is well known to one who is skilled in the art. In some aspect, the first stented valve 10A is suitably connected to the second stented valve 10B. Any conventional means for connecting the two stented valves is applicable, for example, using a wire, a bar, a rod, a coil or the like.

In an alternate embodiment, the venous valve to be placed at either the superior vena cava or the inferior vena cava is a stentless or supportless valve. In still another embodiment, the venous valves are to be implanted by an open chest procedure at the superior vena cava and the inferior vena cava, wherein the valves can be either a stented valve or a stentless valve.

In a preferred embodiment, the stented valve 10A would deploy in the superior vena cava 55 just above the right atrial junction but below the azygos vein, whereas the stented valve 10B would deploy in the inferior vena cava 56 just below the right atrium 52 but above the hepatic veins. In effect, the physiologic changes from the therapy disclosed herein would be to protect the upper and lower body from high or elevated venous pressures. Patients with severe tricuspid regurgitation are troubled by ascites, peripheral edema frequently with stasis changes in the legs, hepatic congestion, which may progress to cardiac cirrhosis and liver dysfunction with prolonged hepatic congestion. Furthermore, high venous pressure may contribute to renal dysfunction and other symptoms of abdominal bloating. The neck vein and upper body congestion is sometimes quite visible in patients including the pulsatile neck veins. By placing the stented valves, it should protect the patient from ascites, hepatic congestion, edema and the eventual development of cardiac cirrhosis.

Figure 3:
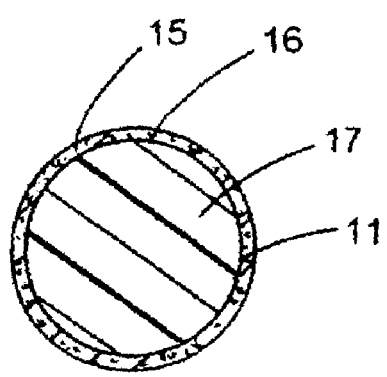
FIG. 3 is a cross-sectional view of the stent strut, section I—I, of the stented valve in FIG. 1.

To enhance the biocompatibility of the device or improved therapy to the surrounding tissue, it is provided a support structure 11 of the stented valve 10 that is coated with a therapeutic agent, wherein the therapeutic agent is selected from a group consisting of anticoagulants, anti-thrombogenic agents, anti-proliferative agents, anti-inflammatory agents, antibiotics, stem cells, growth factors, angiogenesis agents, anti-angiogenesis agents, and statins. The therapeutic agent is to slowly release to the tissue at an effective amount over time. FIG. 3 shows a cross-sectional view of the stent strut 17 of the stent 11, section I—I, of the stented valve 10 in FIG. 1, wherein a polymer layer 16 is coated onto the periphery surface of the stent strut 17 and the polymer layer 16 is loaded with the desired therapeutic agent 15 for slow release at an effective amount over time to the surrounding tissue.

Many medical materials used in the treatment of cardiovascular diseases are required to possess biocompatible and hemo-compatible properties without antigenicity. One method to treat tissue so as to render the tissue more suitable as a biomaterial is a process called chemical treatment. Several chemical treatment agent and methods have been disclosed. Among them, aldehydes (glutaraldehyde, formaldehyde, dialdehyde starch and the like), epoxy compounds, genipin, and their analog or derivatives thereof are all applicable in treating a tissue. Chemical treatment conditions and procedures to render the tissue suitable as a biomaterial depend on the property of each tissue and intended medical applications, wherein the conditions/procedures are well documented in published literature and well known to one who is skilled in the art.

The tissue valve of the stented valve 10 has at least one valve leaflet 13. Sometimes, the tissue valve may have two, three or more leaflets. In some aspect of the present invention, the leaflet 13 is made from a pericardium, the pericardium being selected from a group consisting of a bovine pericardium, an equine pericardium, a porcine pericardium, an ovine pericardium and the like. Further, the tissue valve is chemically treated with a chemical treating agent selected from a group consisting of glutaraldehyde, formaldehyde, dialdehyde starch, epoxy compounds, genipin, and mixture thereof. In one embodiment, the tissue valve is a venous valve selected or procured from a group consisting of a bovine jugular vein, an equine jugular vein, a porcine jugular vein, and an ovine jugular vein. In another embodiment, the tissue valve is a porcine valve.

U.S. Pat. No. 4,806,595 issued on Feb. 21, 1989, entire contents of which are incorporated herein by reference, discloses a novel method for preparing medical materials by using epoxy compounds as chemical treatment agent for tissue, wherein the "epoxy compounds" include glycol diglycidyl ether, polyol polyglycidyl ether, dicarboxylic acid diglycidylester, the analog, and derivatives thereof.

FIG. 4 shows a process or procedure of implanting a stented valve 10A at a superior vena cava 55 and another stented valve 10B at an inferior vena cava 56, wherein both valves are configured to permit blood flow in a direction shown by the arrows 57, 58 towards the right atrium 52.

In some aspect of the invention, it is provided a method of protecting an upper body and a lower body of a patient from high venous pressures comprising implanting a first valve at a superior vena cava and a second valve at an inferior vena cava, wherein the first and second valves are configured to permit blood flow towards a right atrium of the patient and prevent blood flow in an opposite direction. The first valve or the second valve may be a stented or a stentless valve.

Although preferred embodiments of the invention have been described in detail, certain variations and modifications will be apparent to those skilled in the art, including embodiments that do not provide all of the features and benefits described herein. Accordingly, the scope of the present invention is not to be limited by the illustrations or the foregoing descriptions thereof, but rather solely by reference to the appended claims.

What is claimed is:

1. A method of protecting an upper body and a lower body of a patient from high venous pressures comprising implanting a first pericardium tissue valve at a superior vena cava and a second pericardium tissue valve at an inferior vena cava, wherein said first and second valves are configured to permit blood flow towards a right atrium of the patient and prevent blood flow in an opposite direction wherein the first valve is connected to the second valve.

2. The method of claim 1, wherein the first valve or the second valve is a stented valve.

3. The method of claim 1, wherein the step of implanting the first valve at the superior vena cava is by endoluminally delivering said valve through an incision at a blood vessel selected from a group consisting of a jugular vein, a femoral vein, and a subclavian vein.

4. The method of claim 1, wherein the step of implanting the second valve at the inferior vena cava is by endoluminally delivering said valve through an incision at a blood vessel selected from a group consisting of a jugular vein, a femoral vein, and a subclavian vein.

5. The method of claim 1, wherein the step of implanting further comprises first implanting the second pericardium tissue valve at the inferior vena cava followed by implanting the first pericardium tissue valve at the superior vena cava.

6. The method of claim 1, wherein the first pericardium tissue valve and the second pericardium tissue valve are secured to a support structure, wherein said support structure is collapsibly expandable.

7. The method of claim 6, wherein the step of implanting the first or the second valve further comprises passing said support structure through a blood vessel with the support structure in the collapsed position, expanding said support structure at a desired valve location; and securing the tissue valve and the support structure to said desired valve location with the support structure in the expanded shape.

8. The method of claim 6, wherein said support structure is self-expandable.

9. The method of claim 6, wherein said support structure is expandable by positioning an inflatable balloon within said support structure and inflating said balloon.

10. The method of claim 6, wherein said support structure is made of a shape-memory material having a first shape transition temperature of between about 30° C. and 45° C. and a second shape transition temperature of about 5° C. and −10° C., said support structure being collapsibly deformed to below the second shape transition temperature during delivery and expanded after delivery in place upon reaching the first shape transition temperature.

11. The method of claim 6, wherein said support structure is made of a material selected from the group consisting of stainless steel, Nitinol, and plastics.

12. The method of claim 6, wherein said support structure is coated with a therapeutic agent.

13. The method of claim 12, wherein said therapeutic agent is selected from the group consisting of anticoagulants, antithrombogenic agents, anti-proliferative agents, anti-inflammatory agents, antibiotics, stem cells, growth factors, angiogenesis agents, anti-angiogenesis agents, and statins.

14. The method of claim 1, wherein either the first or second pericardium tissue valve includes at least one valve leaflet.

15. The method of claim 6, wherein said support structure further comprises means for anchoring said support structure onto surrounding tissue of either the superior vena cava or the inferior vena cava.

16. The method of claim 6 wherein said support structure comprises a stent.

17. The method of claim 1, wherein the pericardium is selected from the group consisting of a bovine pericardium, an equine pericardium, a porcine pericardium, and an ovine pericardium.

18. The method of claim 1, wherein said first and second pericardium tissue valves are chemically treated with a chemical treating agent selected from the group consisting of glutaraldehyde, formaldehyde, dialdehyde starch, epoxy compounds, genipin, and mixture thereof.

19. The method of claim 1, wherein said first pericardium tissue valve is implanted at the superior vena cava above the right atrial junction but below the azygos vein.

20. The method of claim 1, wherein said second pericardium tissue valve is implanted at the inferior vena cava below the right atrium but above the hepatic veins.

* * * * *